United States Patent [19]

Bollag et al.

[11] 4,021,574

[45] May 3, 1977

[54] ANTIDANDRUFF COMPOSITIONS CONTAINING 9-(4-LOWER ALKOXY-2,3,6-TRILOWER-ALKYL-PHENYL)-3,7-DIMETHYL-NONA-2,4,6,8-TETRAEN-1-OIC ACID LOWER ALKYL AMIDES

[75] Inventors: Werner Bollag, Basel; Rudolf Ruegg, Bottmingen; Gottlieb Ryser, Basel, all of Switzerland

[73] Assignee: Hoffmann-La Roche Inc., Nutley, N.J.

[22] Filed: Sept. 9, 1975

[21] Appl. No.: 611,726

[30] Foreign Application Priority Data

Sept. 24, 1974 Switzerland .................... 12921/74

[52] U.S. Cl. .............................. 424/324; 260/559 R; 424/DIG. 2; 424/DIG. 4; 424/284
[51] Int. Cl.[2] ........................................ A61K 31/165
[58] Field of Search ................ 260/559 R; 424/324, 424/DIG. 4

[56] References Cited

UNITED STATES PATENTS 2,677,697  5/1954  Lott ............................... 260/559 R
3,780,102  12/1973  Bayssat et al. ................. 424/324 X Primary Examiner—Albert T. Meyers
Assistant Examiner—Vera C. Clarke
Attorney, Agent, or Firm—Samuel L. Welt; Bernard S. Leon; R. Hain Swope

[57] ABSTRACT

Compositions suitable for the care of the hair and scalp particularly with respect to the control of dandruff are disclosed. Said compositions comprise a suitable inert carrier and, as an active ingredient, a compound selected from those represented by the formula

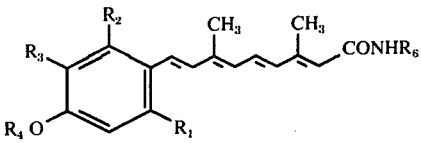

wherein $R_1$, $R_2$, $R_3$, $R_4$ and $R_6$ are lower alkyl.

12 Claims, No Drawings

ANTIDANDRUFF COMPOSITIONS CONTAINING 9-(4-LOWER ALKOXY-2,3,6-TRILOWER-ALKYLPHENYL)-3,7-DIMETHYL-NONA-2,4,6,8-TETRAEN-1-OIC ACID LOWER ALKYL AMIDES

BACKGROUND OF THE INVENTION

In our U.S. patent application Ser. No. 454,007, filed Mar. 22, 1974, now abandoned, compounds represented by the formula

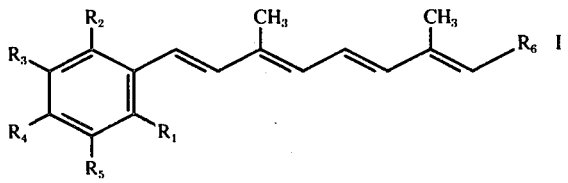

wherein $R_1$ and $R_2$ are lower alkyl; $R_3$ is hydrogen, lower alkyl, lower alkoxy, lower alkenyloxy, nitro, halo, amino, lower alkyl-amino, lower alkanoylamino, or N-heterocyclyl; $R_4$ is hydrogen, lower alkyl, lower alkenyl, lower alkoxy, lower alkenyloxy, nitro, lower alkanoyloxy, amino, lower alkylamino or N-heterocyclyl; $R_5$ is hydrogen, lower alkyl, lower alkenyl, lower alkoxy, lower alkenyloxy, nitro, halo, amino, lower alkanoylamino, lower alkylamino or N-heterocyclyl; with the proviso that at least one of $R_3$, $R_4$, and $R_5$ is other than hydrogen; with the further proviso that when $R_3$ or $R_5$ is halogen, $R_4$ is other than alkoxy; $R_6$ is formyl, hydroxymethylene, alkoxymethylene, alkanoyloxy-methylene, carboxyl, alkoxycarbonyl, alkenloxy-carbonyl, alkynyloxycarbonyl, carbamoyl, mono (lower alkyl)-carbamoyl, di (lower alkyl)-carbamoyl, or N-heterocyclylcarbonyl;
and pharmaceutically acceptable salts thereof are disclosed. Said compounds are disclosed as possessing activity as anti-tumor agents and in the topical and systemic therapy of acne, psoriasis and other related dermatological disorders characterized by an increased or pathologically altered cornification. In accordance with the present invention, it has been found that a select group of compounds falling with the scope of the generic formula given above is particularly efficacious in the control of dandruff.

DETAILED DESCRIPTION OF THE INVENTION

In accordance with the present invention, a method for the control of dandruff is provided which comprises applying to the hair and scalp an effective amount of a composition comprising a suitable, cosmetically acceptable carrier and, as an active ingredient, a compound represented by the formula

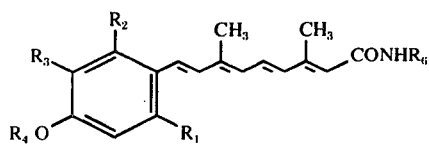

wherein each of $R_1$, $R_2$, $R_3$ $R_4$ and $R_6$ is lower alkyl.
The term "lower alkyl" as utilized herein includes alkyl radicals containing from 1–6 carbon atoms such as, for example, methyl, ethyl, n-propyl, isopropyl or 2-methylpropyl radicals with methyl and ethyl being preferred. A particularly preferred active ingredient of the compositions of the present invention is 9-(4-methoxy-2,3,6-trimethylphenyl)-3,7-nona-2,4,6,8-tetraen-1-oic acid ethyl amide.

The compounds of formula I are prepared by the reaction of a compound represented by the formula

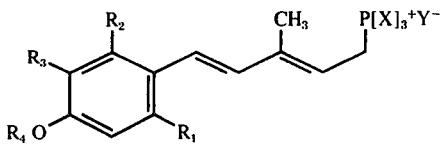

with a compound represented by the formula

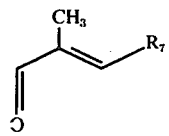

wherein $R_1$, $R_2$, $R_3$ and $R_4$ are as given above, X is aryl, Y is the anionic portion of an organic or inorganic acid and $R_7$ is an alkoxy-carbonyl group
and converting the ester group represented by $R_7$ in the product to the corresponding amide thus yielding the compounds of formula I.

The aryl groups represented by "X" in formula II include all generally known aryl groups. Preferred groups include, for example, mononuclear groups such as phenyl, lower alkyl-substituted phenyl and lower alkoxy-substituted phenyl such as, for example, tolyl, xylyl, mesityl and p-methoxyphenyl. Preferred among the inorganic acid anions represented by "Y" in formula II are chloride, bromide, iodide and hydrosulfate and, of the organic acid anions, the tosyloxy ion is preferred.

The reaction of the compounds represented by formulae II and III is carried out via a Wittig reaction. According to the Wittig procedure, the starting materials are condensed together in the presence of an acid-binding agent, e.g., an alkali metal alcoholate such as sodium methylate or an alkylene oxide which may be alkyl-substituted especially ethylene oxide or 1,2-butylene oxide. The reaction may be carried if desired, in a solvent, e.g., a chlorinated hydrocarbon such as methylene chloride, or dimethylformamide, at a temperature between room temperature and the boiling point of the condensation mixture.

The resulting carboxylic acid ester can be hydrolyzed to a carboxylic acid in a conventional manner such as, for example, by treatment with an alkali, preferably an aqueous-alcoholic solution of sodium hydroxide or potassium hydroxide at a temperature between room temperature and the boiling point of the mixture. The resulting carboxylic acid can then be amidated, for example, by treatment with thionyl chloride to convert it into an acid chloride which can then be converted into an amide by reaction with an appropriate lower alkylamine.

Compounds of formula II are prepared by subjecting the corresponding ($R_1$, $R_2$, $R_3$ and $R_4$O-)-substituted benzene to formylation in the presence of a Lewis acid. Examples of suitable formylating agents include an orthoformic acid ester, formyl chloride and dimethylformamide. Preferred Lewis acids are the halides of zinc, aluminum, titanium, tin and iron such as, for example, zinc chloride, aluminium trichloride, titanium tetrachloride, tin tetrachloride and iron trichloride, as well as the halides of inorganic and organic acids such as, for example, phosphorus oxychloride, methanesulfonyl chloride and the like.

If the formylating agent is present in excess, the formylation may be carried out without the addition of an additional solvent. However, it is preferred to carry out the formylation in an inert solvent such as for example, nitrobenzene, a chlorinated hydrocarbon such as methylene chloride and the like. The reaction is carried out at a temperature between 0° C. and the boiling point of the mixture.

The $R_1$, $R_2$, $R_3$ and $R_4O$-substituted benzaldehydes thus obtained are converted by conventional procedures, for example, by condensation with acetone in the cold, i.e. at a temperature from about 0°–30° C. in the presence of alkali, e.g. dilute aqueous sodium hydroxide to $R_1$, $R_2$, $R_3$, $R_4O$-substituted phenyl-but-3-en-2-one which is in turn converted by conventional procedures, for example, by condensation with acetone in the cold, i.e. at a temperature from about 0°–30° C. in the presence of alkali, e.g. dilute aqueous sodium hydroxide to $R_1$, $R_2$, $R_3$, $R_4O$-substituted phenyl-but-3-en-2-one which is in turn converted by conventional procedures, e.g. an organometallic reaction such as a Grignard reaction with the addition of acetylene, to the corresponding substituted phenyl-3-methyl-3-hydroxypenta-4-en-1-yne. The resulting tertiary acetylene carbinol is then partially hydrogenated conventionally utilizing a partially deactivated noble metal catalyst, i.e., a Lindlar catalyst, to a tertiary ethylenic carbinol which is then converted to the desired phosphonium salt of formula II under allylic rearrangement by treatment with a triarylphosphine, preferably triphenylphosphine, in the presence of a mineral acid such as, for example, sulfuric acid or a hydrogen halide such as, for example, hydrogen chloride or hydrogen bromide in a suitable solvent such as, for example, benzene.

Compounds represented by formula III above can be prepared, for example, by oxidatively cleaving tartaric acid, which may be optionally esterified. The oxidative cleavage may be carried out, for example, with lead tetraacetate at room temperature in an organic solvent such as, for example, benzene. The resulting glyoxalic acid derivative may then be condensed in a known manner with propionaldehyde, conveniently in the presence of an amine at elevated temperature, e.g. between about 60° C. and 110° C. With subsequent water cleavage to yield the desired 3-formyl-crotonic acid derivative.

The antidandruff compositions of the present invention contain in addition to the active ingredient, i.e., a compound of formula I, a pharmaceutically and cosmetically acceptable carrier suitable for application to the hair. Such carriers include, for example, hair lotions and dressings, e.g. gels and shampoos. Generally, hair lotions and dressings comprise aqueous, alcoholic or aqueous/alcoholic solutions, emulsions or gels. Generally, shampoo compositions comprise aqueous detergent bases in liquid or paste form. Such preparations contain conventional additives such as approved coloring agents, perfumes, fillers, thickeners, solvents, opacifiers, builders, conditioners, preservatives, buffers, anti-static agents and the like. It is further preferred in accordance with the invention that such preparations contain an art-recognized bactericidal agent such as, for example, phenoxy-ethanol, hexachlorophene, n-propyl-p-hydroxybenzoate (Nipasol), methyl-p-hydroxybenzoate (Nipagin) and mixtures thereof. The compounds of formula I as well as the aforementioned antibacterial agents are incorporated into the carrier formulations by procedures conventional in the arts of pharmaceutical and cosmetic compounding.

The antidandruff compositions of the present invention contain from about 0.005% by weight to about 0.2% by weight, preferably from about 0.01% by weight to about 0.1% by weight, and most preferably from about 0.05% by weight to about 0.06% by weight of the active ingredient, i.e., the compounds of formula I, when in a hair lotion or hair dressing form. A daily application of such preparations will provide from about 0.25 to about 20 mg. of active ingredient which has been shown to be effective in most instances. The amount of such compositions to be applied to achieve the desired therapeutic result will, of course, vary with the hair of each user, the severity of the dandruff condition and the like.

Shampoo formulations in accordance with the present invention contain from about 0.05% by weight to about 2.0% by weight, preferably from about 0.1% by weight to about 1.0% by weight, most preferably from about 0.5% by weight to about 0.6% by weight active ingredient. Such shampoos provide from about 2.5 mg. to about 200 mg. of active ingredient to the scalp in a normal application. Favorable results have been obtained with applications of such shampoos at as high as 14 day intervals. In most instances, however, such shampoos should be applied more frequently, e.g. at intervals of 4–6 days. This regimen will, as stated above, vary with the individual and the severity of the dandruff condition.

The polyene compounds of formula I have a low toxicity and good skin tolerance. For example, the $LD_{50}$ s.c. in the mouse for 9-(4-methoxy-2,3,6-trimethylphenyl)3,7-nona-2,4,6,8-tetra-en-1-oic acid ethyl amide is greater than 4000 mg/kg after 1, 10 and 20 days in the mouse. As a demonstration of the antidandruff activity of the compounds of formula I, four male volunteers aged 19 to 23 years were treated with 9-(4-methoxy-2,3,6-trimethylphenyl)-3,7-nona-2,4,6,8-tetraen-1-oic acid ethyl amide according to the method described in the Journal of Invest. Dermatology, Vol. 53, p. 107 (1969). Each volunteer was treated by applying to the scalp 15 ml. of 0.1% by weight solution thereof daily for 7 days. The number of corneocytes on the scalp of each subject was determined 1 day before treatment began and 1 day after termination of treatment. The results are given in the following table.

Table

| Volunteer No. | Number of Corneocytes | |
|---|---|---|
| | One day pre-treatment | One day post treatment |
| 1 | 2100 | 1400 |
| 2 | 5100 | 1500 |
| 3 | 3250 | 1600 |
| 4 | 1900 | 1600 |
| Total | 12350 | 6100 |

The above results, averaging as 50% decline in number or corneocytes, establish efficacy of the compositions of the invention in the treatment of dandruff.

The following examples further illustrate the invention. Unless otherwise noted, all temperatures are given in degrees Centigrade.

EXAMPLE 1

The following procedure is illustrative of the synthesis of compounds represented by formula I.

A total of 500 g of 2,3,5-trimethylphenol were introduced into 1840 ml of ethanol and 184 ml of water and treated with 240 g of potassium hydroxide with gentle stirring. 626 Grams of methyl iodide were added to the resulting clear solution at 0°–5° over a period of 30–45 minutes. The mixture was stirred for 2 hours at room temperature, subsequently stirred under reflux conditions at 60° for 12 hours, then treated with 5 liters of water and thoroughly extracted with a total of 6 liters of ether. The extract was washed first with 3 liters of 3-N sodium hydroxide, then twice with 1 liter portions of water, dried over sodium sulfate and evaporated under reduced pressure. The residual 2,3,5-trimethylanisole boiled at 88°–90°/10 Torr after rectification.

184 Grams of phosphorus oxychloride were added dropwise over 20–30 minutes to 87.1 g of dimethylformamide while at 10°–20° with stirring. As the addition neared completion the temperature rose to 25°. 150 Grams of 2,3,5-trimethylaniosole were added over 20 minutes while cooling at 10°–20°. The mixture was slowly heated up to a maximum of 115°, stirred at 100° for 6 hours in order to complete the reaction, cooled, poured into 2 kg of ice/water (1:1) and, after the addition of 1500 ml of benzene, treated with 500 g of sodium acetate. The water phase which formed was separated after stirring for 1 hour and again extracted with 1000 ml of benzene. The combined benzene extracts were washed successively with 480 ml of 1.5-N hydrochloric acid and 500 ml of water, dried over sodium sulfate and filtered over 20 g of decolorizing carbon. The filtrate was evaporated under reduced pressure. The residual 2,3,6-trimethyl-p-anisaldehyde melted at 65°–66° after recrystallization from hexane.

260 Grams of 2,3,6-trimethyl-p-anisaldehyde were introduced into a mixture of 3500 ml of acetone and 1400 ml of water and treated over a period of about 30 minutes with 730 ml of 10% by weight sodium hydroxide solution at 0°–5° with stirring. The mixture was stirred for 3 days at room temperature and, after lowering the pH value to 4–5 by the addition of acetic acid, concentrated under reduced pressure. The concentrate was extracted with a total of 3000 ml of ether. The ether extract was washed first with 700 ml of 5% a aqueous solution of sodium bicarbonate and then with 700 ml of water, dried over sodium sulfate and evaporated under reduced pressure. The residual oily 4-(4-methoxy-2,3,6-trimethylphenyl)-but-3-en-2-one boiled at 120°–127°/0.05 Torr after rectification.

36.45 Grams of magnesium were superficially corroded with a small amount of iodine, introduced into 1000 ml of tetrahydrofuran and treated dropwise under nitrogen within 45 minutes with 162.5 g of ethyl bromide. During the introduction, the temperature rose from an initial temperature of 8°–10° to about 25°. The mixture was stirred until the magnesium had gone completely into, solution an additional solution 5–10 ml of ethyl bromide being added if required to effect solution. The resulting Grignard solution was subsequently added dropwise at 0° to a saturated acetylene-tetrahydrofuran solution prepared by gassing 650 ml of tetrahydrofuran with acetylene over 3 hours at −10° to −5°. The reagent was stirred for 1 hour at 0° and then treated dropwise over 30–45 minutes with a solution of 218 g of 4-(4-methoxy-2,3,6-trimethylphenyl)-but-3-en-2-one in 250 ml of tetrahydrofuran under acetylene gassing at 0°. The mixture was stirred for 24 hours at 0° and subsequently for 12 hours at room temperature, then introduced into 4.5 kg of ice/water (3.5:1), adjusted to a pH of about 4 by the addition of 700 ml of 3-N hydrochloric acid and thoroughly extracted with a total of 3 liters of ether. The ether extract was washed neutral with a total of 2 liters of water, dried over sodium sulfate and filtered over 20 g of decolorizing carbon. The filtrate was evaporated under reduced pressure, the residual 5-(4-methoxy-2,3,6-trimethylphenyl)-3-methyl-3-hydroxy-penta-4-en-1-yne melted at 58° C–60° after rectification at 125°–135°/0.04 Torr.

A total of 244 g of 5-(4-methoxy-2,3,6-trimethylphenyl)-3-methyl-3-hydroxy-penta-4-en-1-yne was dissolved in 400 ml of hexane and, after the addition of 45 g of a partially deactivated palladium catalyst, hydrogenated at room temperature under normal pressure. After about 40–60 minutes and after the uptake of the amount of hydrogen (25 liters) necessary for the saturation of the acetylenic to ethylenic bond, the hydrogenation was terminated. The hydrogenation solution was filtered and filtrate washed with 300 ml of ethyl acetate and evaporated under reduced pressure. The residual 5-(4-methoxy-2,3,6-trimethylphenyl)-3-methyl-3-hydroxy-pent-1,4-diene melted at 46°–47°.

246 Grams of 5-(4-methoxy-2,3,6-trimethylphenyl)-3-methyl-3-hydroxy-penta-1,4-diene were dissolved in 2400 ml of benzene. The solution was treated with 343 g of triphenylphosphine hydrobromide, stirred for 24 hours at 60°, then cooled and separated from the benzene. The sediment was digested four times with 500 ml portions of benzene and, after separation of the benzene washings, dissolved in 700 ml of methylene chloride. The solution was evaporated under reduced pressure. The residual 5-(4-methoxy-2,3,6-trimethylphenyl)-3-methyl-penta-2,4-diene-1-triphenylphosphonium bromide thus obtained was dried under vacuum before further processing.

1775 Grams of lead tetraacetate (90°) were gradually introduced within 30 minutes into a solution of 1000 g of L(+) tartaric acid dibutyl ester in 3850 ml of benzene at 25°–30°. The mixture was subsequently stirred for 1 hour at room temperature. The sediment was filtered off and extracted with 500 ml of benzene. The benzene extract was evaporated under reduced pressure. The residual glyoxalic acid butyl ester boiled at 50°–65°/12 Torr after rectification.

836 Grams of the foregoing glyoxalic acid butyl ester were introduced into 376 g of propionaldehyde. The mixture was treated dropwise with 40.8 g of di(n-butyl)amine at 60°. In so doing, the temperature rose to about 106°. The mixture was then stirred for 2 hours at 106°–111°, cooled and taken up in ether. The ether extract was washed successively with 500 ml of 1-N sulfuric acid, 700 ml of water, 1000 ml of a 5% aqueous solution of sodium bicarbonate and subsequently with 1000 ml of water, dried over sodium sulfate and evaporated under reduced pressure. The residual 3-formylcrotonic acid butyl ester boiled at 93°–105°/14 Torr after rectification.

228 Grams of 5-(4-methoxy-2,3,6-trimethylphenyl)-3-methyl-penta-2,4-diene-1-triphenylphosphonium bromide were introduced into 910 ml of dimethylformamide under nitrogen gassing and treated within 20 minutes with 17.5 g of a suspension of sodium hydride (ca 50%) in mineral oil while cooling to 5°–10°. The mixture was stirred for 1 hour at about 10°, then treated drop-wise with 61.8 g of 3-formyl-crotonic acid butyl ester at 5°–8°, heated for 2 hours at 65°, subsequently introduced into 8 liters of ice-water and, after the addition of 300 g of sodium chloride, thoroughly extracted with a total of 18 liters of hexane. The extract was washed five times with 1 liter positions of methanol/water (6:4) and twice with 1.5 liters portions of water, dried over sodium sulfate and evaporated under reduced pressure. The residual 9-(4-methoxy-2,3,6-trimethylphenyl)-3,7-dimethyl-nona-2,4,6,8-tetraen-1-oic acid butyl ester of melting point 80°–81° was converted into a free acid as follows:

125.8 Grams of 9-(4-methoxy-2,3,6-trimethylphenyl)-3,7-dimethyl-nona-2,4,6,8-tetraen-1-oic acid butyl ester were introduced into 2000 ml of absolute ethanol and treated with a solution of 125.8 g of potassium hydroxide in 195 ml of water. The mixture was heated to boiling for 30 minutes under nitrogen gassing, then cooled, introduced into 10 liters of ice-water and after the addition of ca 240 ml of concentrated hydrochloric acid (pH 2–4), thoroughly extracted with a total of 9 liters of methylene chloride. The extract was washed neutral with about 6 liters of water, dried over calcium chloride and evaporated under reduced pressure. The residue was taken up in 700 ml of hexane. The precipitated 9-(4-methoxy-2,3,6-trimethylphenyl)-3,7-dimethyl-nona-2,4,6,8-tetraen-1-oic acid melted at 228°–230°.

28.6 g of 9-(4-methoxy-2,3,6-trimethylphenyl)-3,7-dimethyl-nona-2,4,6,8-tetraen-1-oic acid were introduced into 300 ml of benzene and treated with 12 g of phosphorus trichloride under nitrogen gassing. The benzene was subsequently distilled off under reduced pressure. The residual 9-(4-methoxy-2,4,6-trimethylphenyl)-3,7-dimethyl-nona-2,4,6,8-tetraen-1-oic acid chloride was dissolved in 1200 ml of ether. The solution was added dropwise at −33° to 500 ml of liquid ethylamine and stirred for 3 hours. The mixture was then diluted with 500 ml of ether and stirred for a further 12 hours without cooling whereby the ammonia evaporated. The residue was dissolved in 10 liters of methylene chloride. The solution was washed twice with 3 liters of water, dried over sodium sulfate and evaporated under reduced pressure. The residual 9-(4-methoxy-2,3,6-trimethylphenyl)-3,7-dimethyl-nona-2,4,6,8-tetraen-1-oic acid ethyl amide melted at 179°–180° after recrystallization from ethanol.

EXAMPLE 2

A hair dressing gel was prepared from the following formulation:

| Ingredient | Amount in Grams |
| --- | --- |
| Rectified alcohol 94% | 37.8 |
| Propyleneglycol | 37.8 |
| Carbopol 940[1] | 1.5 |
| 9-(4-Methoxy-2,3,6-trimethyl-phenyl)-3,7-dimethyl-nona-2,4,6,8-tetraen-1-oic acid ethyl amide | 0.06 |
| Tocopherol (antioxidant) | 0.006 |
| Triethanolamine (10%) | 0.6 |
| Cremophor RH60[2] | 0.3 |
| Suitable Perfume | 0.1 |
| Water qs. ad | 100.00 |

[1]-Carbopol 940 (Trademark) is a carboxyvinyl polymer which serves as a thickening agent.
[2]-Cremophor RH60 (Trademark) is a polyoxyethylene ether of castor oil which serves as a solubilizing agent.

The rectified alcohol and the propyleneglycol were combined and heated to 60° and the Carbopol slowly sprinkled onto the solution with stirring. The mixture was stirred until all ingredients were in solution. The essential active ingredient was added and the mixture stirred until complete solution was achieved. After cooling to 40°, the tocopherol, Cremophor and perfume were added. The triethanolamine was mixed with the water and added. The resulting mixture was stirred until homogeneous.

EXAMPLE 3

A shampoo was prepared from the following formulation:

| Ingredient | Amount in Grams |
| --- | --- |
| Texapon EVR[1] | 40.00 |
| Komperlan KD[2] | 4.00 |
| 9-(4-Methoxy-2,3,6-trimethyl-phenyl)-3,7-dimethyl-nona-2,4,6,8-tetraen-1-oic acid ethyl amide | 0.50 |
| Perfume | 0.40 |
| Nipagin (methyl-p-hydroxybenzoate) | 0.18 |
| Nipasol (n-propyl-p-hydroxybenzoate) | 0.02 |
| Water qs. ad | 100.00 |

[1]-Texapon EVR (Trademark) sodium lauryl ether sulphate; active detergent: 35 – 37%.
[2]-Komperlan KD (Trademark) Coconut oil acid diethanolamide (about 90% amide content)

The active ingredient was dissolved in the Komperlan at 80° and added to the Texapon also warmed to 80°. The resulting finely dispersed suspension was treated with hot water (80°) and slowly cooled while stirring. The perfume, the Nipagin and the Nipasol were added at 40°. to yield a highly viscous shampoo.

EXAMPLE 4

A hair and scalp antiseptic wash lotion was prepared from the following formulation:

| Ingredient | Amount in Grams |
| --- | --- |
| Rectified alcohol 94% | 50 |
| 9-(4-Methoxy-2,3,6-trimethylphenyl)-3,7-dimethyl-nona-2,4,6,8-tetraen-1-oic acid ethyl amide | 0.06 |
| Cremophor RH60 | 0.3 |
| Water qs. ad | 100.00 |

The essential active ingredient and the Cremophor were dissolved in the rectified alcohol. The solution was made up with water to 100 ml.

We claim:

1. A composition for application to the hair and scalp for the treatment of dandruff comprising a pharmaceutically acceptable hair lotion or dressing containing, as an active ingredient, from about 0.005% by weight to about 0.2% by weight of a compound represented by the formula

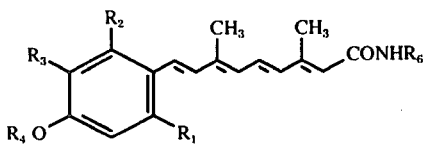

wherein $R_1$, $R_2$, $R_3$, $R_4$ and $R_6$ are lower alkyl.

2. The composition in accordance with claim 1 wherein said active ingredient is present in from about 0.01% by weight to about 0.1% by weight.

3. The composition in accordance with claim 1 wherein said active ingredient is present in from about 0.05% by weight to about 0.06% by weight.

4. The composition in accordance with claim 1 wherein said active ingredient is 9-(4-methoxy-2,3,6-trimethylphenyl)-3,7-nona-2,4,6,8-tetraen-1-oic acid ethyl amide.

5. A method for the treatment of dandruff which comprises applying to the scalp of an individual requiring such treatment an effective amount of the composition of claim 1.

6. The method in accordance with claim 5 wherein a sufficient amount of said composition is applied to the scalp to provide from about 0.25 mg to about 20 mg of said active ingredient.

7. A composition for application to the hair and scalp for the treatment of dandruff comprising a pharmaceutically acceptable shampoo containing, as an active ingredient, from about 0.05% by weight to about 2.0% by weight of a compound represented by the formula

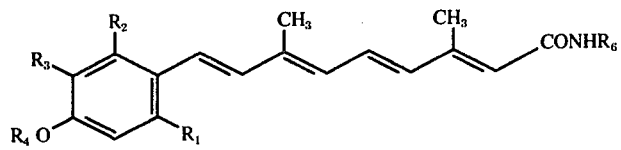

wherein $R_1$, $R_2$, $R_3$, $R_4$ and $R_6$ are lower alkyl.

8. The composition in accordance with claim 7 wherein said active ingredient is present in from about 0.1% by weight to about 1.0% by weight.

9. The composition in accordance with claim 7 wherein said active ingredient is present in from about 0.5% by weight to about 0.6% by weight.

10. The composition in accordance with claim 7 wherein said active ingredient is 9-(4-methoxy-2,3,6-trimethylphenyl)-3,7-nona-2,4,6,8-tetraen-1-oic acid ethyl amide.

11. A method for the treatment of dandruff which comprises applying to the scalp of an individual requiring such treatment an effective amount of the composition of claim 7.

12. The method in accordance with claim 11 wherein a sufficient amount of said composition is applied to the scalp to provide from about 2.5 mg to about 200 mg of said active ingredient.

* * * * *